United States Patent [19]
Nicolau et al.

[11] Patent Number: 6,072,078
[45] Date of Patent: Jun. 6, 2000

[54] VINYL ACETATE PRODUCTION USING A CATALYST COMPRISING PALLADIUM, GOLD, COPPER AND ANY OF CERTAIN FOURTH METALS

[75] Inventors: Ioan Nicolau; Philip M. Colling, both of Corpus Christi, Tex.

[73] Assignee: Celanese International Corporation, Dallas, Tex.

[21] Appl. No.: 08/989,886

[22] Filed: Dec. 12, 1997

[51] Int. Cl.[7] ................................................ C07C 67/05
[52] U.S. Cl. ............................................................ 560/245
[58] Field of Search ............................................. 560/245

[56] References Cited

U.S. PATENT DOCUMENTS

| | | | |
|---|---|---|---|
| 3,190,912 | 6/1965 | Robinson | 560/245 |
| 3,658,888 | 4/1972 | Hornig et al. | 560/245 |
| 3,743,607 | 7/1973 | Sennewald | 502/170 |
| 4,048,096 | 9/1977 | Bissot | 502/170 |
| 4,087,622 | 5/1978 | Nakamura et al. | 560/245 |
| 4,119,567 | 10/1978 | Bartsch | 502/170 |
| 4,158,737 | 6/1979 | Bartsch | 560/245 |
| 4,764,498 | 8/1988 | Wissner et al. | 502/251 |
| 5,332,710 | 7/1994 | Nicolau et al. | 560/245 |
| 5,347,046 | 9/1994 | White et al. | 560/245 |
| 5,567,839 | 10/1996 | Gulliver et al. | 560/245 |
| 5,576,457 | 11/1996 | Abel | 560/245 |
| 5,674,800 | 10/1997 | Abel et al. | 502/326 |
| 5,688,993 | 11/1997 | Provine | 560/245 |

*Primary Examiner*—Gary Geist
*Assistant Examiner*—Robert W. Deemie
*Attorney, Agent, or Firm*—M. Susan Spiering

[57] ABSTRACT

A catalyst for the production of vinyl acetate by reaction of ethylene, oxygen and acetic acid as reactants comprising a porous support on the porous surfaces of which is deposited catalytically effective amounts of metallic palladium and gold, copper as the free metal or cupric acetate, and a fourth metal selected from the group consisting of magnesium calcium, barium, and zirconium, as its oxide or mixture of oxide and free metal.

8 Claims, No Drawings

VINYL ACETATE PRODUCTION USING A CATALYST COMPRISING PALLADIUM, GOLD, COPPER AND ANY OF CERTAIN FOURTH METALS

BACKGROUND OF THE INVENTION

1. Field of the Invention

This invention relates to new and improved catalysts for the production of vinyl acetate by reaction of ethylene, oxygen and acetic acid.

2. Background Information Including Description of Related Art

It is known to produce vinyl acetate by reaction of ethylene, oxygen and acetic acid using a catalyst consisting of palladium, gold, and copper supported on a carrier. While the process utilizing such a catalyst is capable of producing vinyl acetate at relatively high levels of productivity, any expedient which could possibly result in even greater productivity would be very desirable.

The following references may be considered material to the invention claimed herein.

U.S. Pat. Nos. 3,775,342 issued Nov. 27, 1973, and 3,822,308 issued Jul. 2, 1974, both to Kronig et al., each discloses a method of making vinyl acetate catalysts comprising treating a support simultaneously or successively with a solution A containing dissolved salts of noble metals such as palladium and gold and a solution B containing compounds able to react on the support with the noble metal salts to form water insoluble compounds, treating such water-insoluble compounds with a reducing agent to convert the water-insoluble noble metal compounds to the free metals, washing the catalyst to remove water-soluble compounds, and applying an alkali metal compound e.g. an alkali metal carboxylate before or after treatment with the reducing agent. Solution A can optionally also contain salts of other metals such as magnesium, calcium, barium and copper.

U.S. Pat. No. 5,332,710, issued Jul. 26, 1994, to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as a insoluble compounds on the support by immersing and tumbling the impregnated support in a reactive solution for at least ½ hour to precipitate such compounds, and subsequently reducing the compounds to free metallic form.

U.S. Pat. No. 5,347,046, issued Sep. 13, 1994 to White et al., discloses catalysts for the production of vinyl acetate by reaction of ethylene, oxygen, and acetic acid, comprising a palladium group metal and/or a compound thereof, gold and/or a compound thereof, and copper, nickel, cobalt, iron, manganese, lead or silver, or a compound thereof, preferably deposited on a support material.

U.S. Pat. No. 5,567,839, issued Oct. 22, 1996, to Gulliver et al., discloses a method of producing vinyl acetate catalysts including the step of using a barium "salt", such as barium hydroxide, to precipitate water-insoluble palladium and gold compounds onto a support prior to reduction with a reducing agent. When barium hydroxide is used as precipitant, residual barium remains in the finished catalyst.

SUMMARY OF THE INVENTION

In accordance with this invention, a catalyst is provided useful for the production of vinyl acetate by reaction of ethylene, oxygen and acetic acid, comprising a porous support on the porous surfaces of which is deposited catalytically effective amounts of metallic palladium and gold, copper as free metal or cupric acetate, and a fourth metal selected from the group consisting of magnesium, calcium, barium, and zirconium, as its oxide or mixture of oxide and free metal, with any of the latter metals being hereinafter referred to as a "fourth" metal.

It is believed that vinyl acetate catalysts under the invention containing catalytically effective amounts of palladium, gold, copper and any of the specified fourth metals perform with relatively high activity and/or low selectivity to $CO_2$ and/or heavy ends, such that the use of such catalysts often result in greater vinyl acetate productivity than when any of various catalysts known in the art is employed.

DETAILED DESCRIPTION OF THE INVENTION

In preparing the catalysts under this invention, the catalyst support material is composed of particles having any of various regular or irregular shapes, such as spheres, tablets, cylinders, rings, stars, or other shapes, and may have dimensions such as diameter, length, or width of about 1 to about 10 mm., preferably about 3 to 9 mm. Spheres having a diameter of about 4 to about 8 mm. are preferred. The support material may be composed of any suitable porous substance, e.g., silica, alumina, silica-alumina, titania, zirconia, silicates, aluminosilicates, titanates, spinel, silicon carbide, or carbon and the like.

The support material may have a surface area within the range, for example, of about 10 to about 350, preferably about 100 to about 200 $m^2/g$, an average pore size in the range, for example, of about 50 to about 2000 angstroms, and a pore volume in the range, for example, of about 0.1 to 2, preferably about 0.4 to about 1.2 ml/g.

In the preparation of the catalysts of this invention, the support material may be treated to deposit catalytic amounts of palladium, gold, copper and fourth metal on the porous surfaces of the support particles. Any of various methods for accomplishing this purpose may be used, all of which involve simultaneous or separate impregnations of the support with one or more aqueous solutions of water-soluble compounds of the catalytically active metals. Palladium(II) chloride, sodium palladium(II)chloride, potassium palladium(II)chloride, palladium(II)nitrate or palladium(II) sulfate are examples of suitable water-soluble palladium compounds; an alkali metal, e.g., sodium or potassium salt of auric(III)chloride or tetrachloroauric(III)acid can be used as the water-soluble gold compound; and cupric nitrate trihydrate or hexahydrate, cupric chloride (anhydrous or dihydrate), cupric acetate monohydrate, cupric sulfate (anhydrous or pentahydrate), cupric bromide, or cupric formate (anhydrous or tetrahydrate), can be used as the water-soluble copper compound. Depending on which fourth metal is desired in the catalyst, the following water-soluble salts are examples of compounds which can be used for the impregnation of such fourth metal: magnesium sulfate (anhydrous or hydrated), magnesium acetate (anhydrous or hydrated), magnesium chloride (anhydrous or hydrated), or magnesium nitrate (hydrated); calcium chloride (anhydrous or hydrated), calcium acetate (anhydrous or monohydrate), or calcium nitrate (anhydrous or hydrated); barium acetate (anhydrous or hydrated), or barium nitrate (anhydrous); or zirconium sulfate tetrahydrate, zirconium chloride, or zirconium nitrate (anhydrous or pentahydrate). An alkali metal salt of tetrachloroauric(III)acid, sodium palladium(II)chloride and cupric nitrate trihydrate or cupric chloride are preferred salts for impregnation of gold, palladium and copper respectively because of their good water solubility.

In preparing the catalyst, the impregnations of the support material with solutions of water-soluble salts of the catalytically active metals may be effected by any method known to those skilled in the art. Preferably, however, such impregnations are accomplished by the "incipient wetness" method wherein an amount of water-soluble salt solution used for the impregnation is from about 95 to about 100 percent of the absorptive capacity of the support material. The concentration of the solution or solutions is such that the amounts of catalytically active metals in the solution or solutions absorbed on the support is equal to a desired predetermined amount. If more than one such impregnation is carried out, then each impregnation may contain water-soluble compound equivalent to all or only a portion of the amount of one or any combination of the four catalytically active metals desired in the final catalyst, as long as the amounts of such metals in the total of the impregnating solutions absorbed are equal to the final desired amounts. In particular, it may be desirable to impregnate the support with more than one solution of a water-soluble gold compound, as more fully described hereinafter. The impregnations are such as to provide, for example, about 1 to about 10 grams of elemental palladium; for example, about 0.5 to about 10 grams of elemental gold; and, for example about 0.5 to about 3.0 grams of elemental copper per liter of finished catalyst, with the amount of gold being from about 10 to about 125 weight percent based on the weight of palladium. Depending on which fourth metal is desired in the catalyst and assuming such fourth metal is the only one present, the number of grams of elemental fourth metal per liter of catalyst provided by the impregnation may be, for example, within the following ranges.

magnesium: about 0.1 to about 2.0, preferably about 0.3 to about 1.0;

calcium: about 0.2 to about 4.0; preferably about 0.5 to about 1.5;

barium: about 0.2 to about 5.0, preferably about 0.6 to about 3.0;

zirconium: about 0.4 about to 7.0, preferably about 1.0 to about 3.0;

After each impregnation of the support with an aqueous solution of water-soluble salt of a catalytically active metal, the metal is "fixed", i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkaline compound should be in an amount of, for example, about 1 to about 2, preferably about 1.1 to about 1.8 times the amount necessary to completely precipitate the cations of the catalytically active metals present in the water-soluble salts. The fixing of the metal may be done by the incipient wetness method wherein the impregnated support is dried, e.g., at a temperature of about 150° C. for one hour, contacted with an amount of solution of the alkaline material equal to about 95–100% of the pore volume of the support, and allowed to stand for a period of about ½ hour to about 16 hours; or the roto-immersion method wherein the impregnated support without drying is immersed in a solution of the alkaline material and is rotated and/or tumbled during at least the initial period of precipitation such that a thin band of the precipitated water-soluble compound is formed at or near the surface of the support particles. In carrying out the fixing of metals by roto-immersion, the rotation and tumbling may be carried out, for example, at about 1 to about 10 rpm for a period of, for example, at least about 0.5 hour, preferably about 0.5 to about 4 hours. The contemplated roto-immersion method is disclosed in previously cited U.S. Pat. No. 5,332,710, the entire disclosure of which is incorporated herein by reference.

The fixed, i.e., precipitated palladium, gold, copper and fourth metal compounds may be reduced, for example, in the vapor phase with ethylene, e.g., about 5% in nitrogen at about 150° C. for about 5 hours after first washing the catalyst containing the fixed metal compounds, until it is free of anions such as halide, and drying, e.g., at about 150° C. for about 1 hour, or such reduction may be accomplished before washing and drying in the liquid phase at room temperature with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed metal compounds present on the support may be employed as conventional in the art. The reduction of the fixed palladium, gold and copper compounds mainly results in the formation of the free metal, although a minor amount of metal oxide may also be present, while the reduction of the fixed fourth metal generally results in the formation of an oxide or a mixture of oxide and free metal, depending on reduction conditions and which fourth metal is present. In preparations using more than one impregnation and fixing steps, the reduction may be carried out after each fixing step or after the total of the metallic elements have been fixed on the support.

As an example of foregoing general procedure, a "separate fix" method may be used to fix the catalytically active metallic elements on the support and reduce the water-insoluble metal compounds to the desirable free metallic form. In this method, using the specific procedures described previously, the support is first impregnated with an aqueous solution of water-soluble compounds of palladium, copper, and fourth metal by incipient wetness, and the palladium, copper, and fourth metal are then fixed by treatment with an alkaline fixing solution by incipient wetness or roto-immersion, preferably roto-immersion. The catalyst is then dried and separately impregnated with a solution of a soluble gold compound having the amount of elemental gold desired in the catalyst, and the gold is fixed by treatment with an alkaline fixing solution by incipient wetness or roto-immersion, preferably incipient wetness. If the gold is to be fixed by the incipient wetness method, such fixing may be combined with the impregnation step by using a single aqueous solution of soluble gold compound and alkaline fixing compound in an amount in excess of that necessary to convert all the gold in the solution to a fixed insoluble gold compound, e.g., auric hydroxide. If a hydrocarbon such as ethylene, or hydrogen is to be used in the vapor phase as reducing agent, the catalyst containing the fixed metal compounds is washed until it is free of dissolved anions, dried, and reduced with ethylene or other hydrocarbon, or hydrogen, as previously described. If hydrazine is to be used in the liquid phase as reducing agent, the catalyst containing the fixed metal compounds is treated with an aqueous solution of excess hydrazine hydrate before washing and drying to reduce the metal compounds to the free metals, and the catalyst is then washed and dried as described.

Another alternate method of preparing the catalyst is a "modified roto-immersion" method, in which only part of the gold is impregnated with the palladium, copper and fourth metal in a first impregnation, the metals are fixed by reaction with an alkaline fixing compound by roto-immersion, the fixed metal compounds are reduced to the free metals, e.g., with ethylene or hydrazine hydrate, with washing and drying done before an ethylene reduction or after a hydrazine reduction. The catalyst is then impregnated with the remainder of the gold which is fixed on the catalyst using any of the procedures described previously. Preferably the impregnation and fixing are accomplished in a single step by incipient wetness using a single solution of a water-soluble gold compound and an appropriate alkaline compound. The added, fixed gold is then reduced, e.g., with ethylene or hydrazine, after or before washing and drying, as described previously.

Not wishing to be bound by theory, it is believed that an advantageous variant of the catalyst of this invention comprises a porous support on the porous surfaces of which is deposited metallic copper in a zone surrounded by deposits of catalytically effective amounts of metallic palladium, gold, and fourth metal, none of which is substantially intermingled with said copper. This catalyst may be prepared using various techniques of impregnation, fixing and reduction as described hereinbefore. The use of this catalyst in which the zone of copper is surrounded by the palladium, gold and fourth metal and the copper is therefore less exposed to ambient reactor conditions, contributes to a reduction in the loss of copper by volatilization.

Another useful variant of the catalyst of this invention comprises a porous support on the porous surfaces of which are deposited catalytically effective amounts of metallic palladium and gold, the fourth metal as oxide or mixture of oxide and free metal, and copper as cupric acetate. This catalyst variant is made by first preparing a catalyst precursor comprising a porous support on the porous surfaces of which are deposited catalytically effective amounts of metallic palladium and gold, and a fourth metal as its oxide, or mixture of oxide and free metal using any of the techniques of impregnation, fixing and reduction described previously. The catalyst precursor is then impregnated with an aqueous solution of cupric acetate, either monohydrate or anhydrous, preferably by incipient wetness. The catalyst is then dried such that the finished catalyst contains cupric acetate in an amount equivalent to, for example, about 0.3 to about 5.0 grams, preferably about 0.5 to about 3.0 grams of elemental copper per liter of finished catalyst After the catalyst containing palladium, gold and copper in free metallic form and fourth metal as oxide or mixture of oxide and free metal, deposited on a support material, is prepared by any of the foregoing methods, it is advantageously further impregnated with a solution of an alkali metal acetate, preferably potassium or sodium acetate, and most preferably potassium acetate. The catalyst is then dried such that the finished catalyst contains, for example, about 10 to about 70, preferably about 20 to about 60 grams of alkali metal acetate per liter of finished catalyst. When the catalyst variant is being prepared in which the copper is present as cupric acetate, the optional impregnation of the catalyst with alkali metal acetate, when carried out, may be accomplished before or after the impregnation with cupric acetate. Preferably, however, the alkali metal acetate impregnation is combined with that of cupric acetate, i.e., the catalyst containing metallic palladium and gold, and fourth metal as oxide or mixture of oxide and free metal, is impregnated simultaneously with a single solution of both cupric acetate and alkali metal acetate to yield a finished catalyst which after drying contains the desired amounts of both acetates.

While the catalysts of this invention have been described containing only one "fourth" metal, more than one of such metals can actually be present. When at least two of such described "fourth" metals are desired in the catalyst, the initial impregnating solution will contain dissolved salts of these metals to provide such metals in the finished catalyst within ranges, the upper and lower limits of each of which is a fraction of the limits defined previously on the assumption that only a single "fourth" metal is present, such fraction being the same as the fraction that the individual "fourth" metal is of the total amount of fourth metal in the catalyst.

When vinyl acetate is prepared using a catalyst according to the present invention, a stream of gas, which contains ethylene, oxygen or air, acetic acid, and desirably an alkali metal acetate, is passed over the catalyst. The composition of the gas stream can be varied within wide limits, taking into account explosive limits. For example, the molar ratio of ethylene to oxygen can be about 80:20 to about 98:2, the molar ratio of acetic acid to ethylene can be about 100:1 to about 1:100, preferably about 10:1 to about 1:10 and most preferred about 1:1 to about 1:8 and the content of gaseous alkali metal acetate can be about 1–100 ppm, relative to the acetic acid employed. The alkali metal acetate may be conveniently added to the feed stream as a spray of an aqueous solution of such acetate. The gas stream also can contain other inert gases, such as nitrogen, carbon dioxide and/or saturated hydrocarbons. Reaction temperatures which can be used are elevated temperatures, preferably those in the range of about 150–220° C. The pressure employed can be a somewhat reduced pressure, normal pressure or elevated pressure, preferably a pressure of up to about 20 atmospheres gauge.

An advantageous variant of a process for producing vinyl acetate using the catalyst of this invention is the inclusion of a non-halogen containing copper compound in the feed stream of reactants to the process. The non-halogen containing copper compound is preferably somewhat water soluble or acetic acid soluble and may be, for example cupric acetate (anhydrous or monohydrate) which is preferred, cupric nitrate trihydrate or hexahydrate, cupric sulfate (anhydrous or pentahydrate), or cupric formate (anhydrous or pentahydrate) and the like. The amount of the copper compound fed to the reaction can be such as to provide, for example, about 10 ppb (parts per billion) to about 50 ppm (parts per million), preferably about 20 ppb to about 10 ppm of elemental copper relative to acetic acid in the feed stream. By means of this feature, the amount of copper in the cupric acetate of the catalyst lost by the catalyst volatilization during long term use is reduced, than when no copper compound is included in the feed.

The following non-limiting examples further illustrate the invention.

COMPARATIVE EXAMPLE A AND EXAMPLES 1 TO 3

These examples illustrate the preparation of catalysts under the invention by the "separate fix" method, and the advantages of such catalysts in the production of vinyl acetate in terms of higher activity and/or lower heavy ends selectivity.

In Comparative Example A which served as a control, a support material consisting of Sud Chemie KA-160 silica spheres having a nominal diameter of 5 mm., a surface area of about 160 to 175 $m^2/g$, and a pore volume of about 0.68 ml/g., was first impregnated by incipient wetness with an aqueous solution of sodium palladium(II)chloride and cupric chloride sufficient to provide about 7 grams of elemental palladium and 1.39 grams of elemental copper per liter of catalyst. The palladium and copper were then fixed to the support as palladium(II)hydroxide and cupric hydroxide by treating the catalyst by roto-immersion with an aqueous sodium hydroxide solution such that the Na/Cl molar ratio was about 1.2:1. The catalyst was then dried at 100° C. for 1 hour in a fluid bed drier following which it was impregnated by incipient wetness with an aqueous solution of sodium tetrachloroaurate in an amount sufficient to provide the catalyst with 4 grams/liter of elemental gold, and sodium hydroxide such that the Na/Cl mole ratio was about 1.8:1, to fix the gold on the support as auric hydroxide. The catalyst was then water washed until chloride free (about 5 hours) and dried at 150° C. for one hour in nitrogen flow. The palladium and auric hydroxides were then reduced to the free metals by contacting the catalyst with ethylene (5% in nitrogen) in the vapor phase at 150° C. for 5 hours. Finally the catalyst was impregnated by incipient wetness with an aqueous solution of potassium acetate in an amount sufficient to provide 40 grams of potassium acetate per liter of catalyst, and dried in a fluid bed drier at 100–150° C. for one hour.

In Examples 1 to 3, the procedure of Comparative Example A was followed except that the solution of sodium palladium(II)chloride and cupric chloride contained in addition varying amounts of a dissolved salt of a fourth metal which was subsequently fixed on the support as the hydroxide together with the palladium(II) and cupric hydroxides and reduced with ethylene to the oxide or mixture of oxide and free metal together with the free metallic palladium, copper and gold. The fourth metal salts were, respectively, calcium chloride (Example 1), barium chloride (Example 2), and zirconium sulfate (Example 3).

The catalysts prepared as described in Comparative Example A and Examples 1–3 were tested for their activity in the production of vinyl acetate by reaction of ethylene, oxygen and acetic acid. To accomplish this, about 60 ml of each type of catalyst prepared in the examples were placed in separate stainless steel baskets. The temperature of each basket was measured by a thermocouple at both the top and bottom of each basket. Each reaction basket was placed in a Berty continuously stirred tank reactor of the recirculating type and was maintained at a temperature which provided about 45% oxygen conversion with an electric heating mantle. A gas mixture of about 130 l/hr (measured at N.T.P.) of ethylene, about 26 l/hr of oxygen, about 128 l/hr of nitrogen, about 130 g/hr of acetic acid, and about 2 mg/hr of potassium acetate, was caused to travel under pressure at about 12 atmospheres through each basket. The reaction was terminated after about 18 hours. Analysis of the products was accomplished by on-line gas chromatographic analysis combined with off-line liquid product analysis by condensing the product stream at about 10° C. to obtain optimum analysis of the end products.

Table I shows for each example the identity and amount in grams per liter of catalyst of the elemental fourth metal as the oxide or mixture of oxide and free metal in the catalyst (4th Met., g/L) in addition to the 7 g/L of palladium, 4 g/L of gold, and 1.39 g/L of copper, and the results of the analysis of the reaction product in terms of percent selectivity of $CO_2$ ($CO_2$, % Sel.) and heavy ends, (HE, % Sel.) and relative activity of the reaction expressed as an activity factor (Act.) which is computer calculated in the following way: The computer program uses a series of equations that correlates the activity factor with the catalyst temperature (during the reaction), oxygen conversion, and a series of kinetic parameters for the reactions that take place during vinyl acetate synthesis. More generally, the activity factor is inversely related to the temperature required to achieve constant oxygen conversion.

TABLE I

| Example | 4th Met, g/L | $CO_2$ % Sel. | HE % Sel. | Act. |
|---|---|---|---|---|
| A | — | 7.76 | 1.34 | 1.92 |
| 1 | Ca, 0.88 | 7.67 | 1.08 | 1.93 |
| 2 | Ba, 3.0 | 8.05 | 1.25 | 2.05 |
| 3 | Zr, 2.0 | 7.66 | 0.93 | 1.85 |

COMPARATIVE EXAMPLE B AND EXAMPLES 4 TO 6

In these examples the procedure of Comparative Example A and Examples 1 to 3 were followed respectively, except that the nominal diameter of the silica sphere support material was 7 rather than 5 mm. Table II gives the results of these experiments which in Examples 4 and 5 are each averages of two experiments run with the same catalyst under identical conditions.

TABLE II

| Example | 4th Met, g/L | $CO_2$, % Sel. | HE, % Sel. | Act. |
|---|---|---|---|---|
| B | — | 8.19 | 1.45 | 1.98 |
| 4 | Ca, 0.88 | 9.01 | 1.27 | 2.09 |
| 5 | Ba, 3.0 | 8.86 | 1.26 | 2.05 |
| 6 | Zr, 2.0 | 9.86 | 1.26 | 2.22 |

The results of the foregoing experiments as shown in Tables I and II indicate that the addition of calcium, barium or zirconium to an otherwise identical palladium-gold-copper catalyst prepared by the separate fix method reduces the heavy ends selectivity and/or increases the activity factor of the catalyst when used to produce vinyl acetate from ethylene and acetic acid under substantially identical conditions.

EXAMPLES 7 TO 12

These examples illustrate the preparation of catalysts according to the present invention by the "modified roto-immersion" method and the results of the use of such catalysts in vinyl acetate production, in the same terms as those shown for the catalysts of Examples 1–6.

The same support as used in Comparative Example A and Examples 1–3 was first impregnated by the incipient wetness method with a solution of palladium, gold, copper and fourth metal salts sufficient to provide 7 grams of elemental palladium, 4 grams of elemental gold, 1.9 grams of elemental copper and varying amounts of the elemental fourth metal. The palladium, gold and copper salts used were the same as in the previous examples, and the fourth metal salts were zirconium sulfate in Examples 7 and 8, barium chloride in Example 9, calcium chloride in Example 10 and magnesium sulfate in Examples 11 and 12. The metals were then fixed by roto-immersion in an aqueous solution of about 120% of the amount of sodium hydroxide necessary to precipitate the palladium, gold, copper and fourth metal, and the latter metals were reduced either with ethylene in the vapor phase (5% in nitrogen) at about 150° C. for about 5 hours, or in the liquid phase using an aqueous solution of hydrazine hydrate at an excess weight ratio of hydrazine to metals of 12:1. After the reduction, the catalyst was washed until chloride free (about 5 hours), dried at 100° C. for 1 hour in a fluid drier, and then impregnated by incipient wetness with an aqueous solution of gold salt sufficient to provide the catalyst with 3 additional grams per liter of elemental gold (for a total of 7), and sodium hydroxide such that the Na/Cl mole ratio was about 1.8:1, to fix the additional gold. The additional gold was then reduced with the same reducing agent as used in the first reduction, as described previously, and the catalyst was washed, dried, and impregnated with potassium acetate as described in Comparative Example A. The catalyst was then tested for its function in the production of vinyl acetate as described in the previous examples.

Table III gives the identity and amount of fourth metal in the catalyst in addition to the about 7 g/L each of palladium and gold, and 1.9 g/L of copper, the results of the reaction in terms of percent selectivity to $CO_2$ and heavy ends, and the activity factor, all as shown in Tables I and II, and in addition, whether the reducing agent (Red. Agent) is ethylene ($C_2H_2$) or hydrazine ($N_2H_4$). The reaction results of Examples 7 to 11 are for each example, averages of the results of two experiments run with the same catalyst under identical conditions.

TABLE III

| Example | 4th Met, g/L | Red. Agent | $CO_2$, % Sel. | HE, % Sel. | Act. |
|---|---|---|---|---|---|
| 7  | Zr, 2.0  | $C_2H_4$ | 7.43 | 0.92 | 1.94 |
| 8  | Zr, 2.0  | $N_2H_4$ | 8.29 | 1.12 | 2.28 |
| 9  | Ba, 3.0  | $N_2H_4$ | 8.23 | 1.1  | 2.27 |
| 10 | Ca, 0.88 | $N_2H_4$ | 8.33 | 1.16 | 2.27 |
| 11 | Mg, 0.53 | $N_2H_4$ | 8.03 | 1.12 | 2.26 |
| 12 | Mg, 0.53 | $C_2H_4$ | 7.98 | 0.95 | 1.59 |

The results of Table III indicate that the fourth metal-containing catalysts of this invention prepared by the modified roto-immersion method functioned in the production of vinyl acetate from ethylene, acetic acid and oxygen with relatively low $CO_2$ and heavy ends selectivities.

EXAMPLE 13

This example illustrates the preparation by the modified roto-immersion method, and results of the use of a catalyst containing magnesium as a fourth metal which is similar to that of Example 11 except that it contains about 4 rather than about 7 grams/liter of gold.

The procedure of Example 11 was followed using hydrazine as reducing agent, except that only enough sodium tetrachloroaurate was present in each of the two impregnating solutions to provide 2 grams/liter of gold to the catalyst for a total of 4 grams/liter in the final catalyst When tested in the production of vinyl acetate as described in the previous examples, the product stream exhibited a carbon dioxide selectivity of 9.51%, a heavy ends selectivity of 0.72% which is particularly low, and an activity factor of 1.87.

EXAMPLE 14

This example illustrates the preparation and results of the use of a catalyst in which palladium, gold, and magnesium are deposited on a metallic copper containing support material by the modified roto-immersion method such that there is substantially no intermingling of copper with the other metals. It is believed that the copper on the support material is surrounded by and not intermingled with the other metals. This in turn minimizes the loss of copper by volatilization.

A support material as described in comparative Example A in which the spheres had a nominal diameter of 7 mm, was impregnated by the incipient wetness method with an aqueous solution of cupric nitrate trihydrate sufficient to provide the catalyst with about 1.9 grams/liter of elemental copper. Without drying, the copper was fixed on the support by treating the support by roto-immersion with an aqueous solution of sodium hydroxide containing about 120% of the amount of sodium hydroxide needed to convert the copper to cupric hydroxide. The fixed cupric hydroxide-containing support was then water washed until free of anions, dried at a temperature of 100° C. for 1 hour in a fluid bed drier, calcined by heating in air at about 200° C. for about 18 hours, and the cupric hydroxide reduced to metallic copper in the vapor phase by contact with ethylene (5% in nitrogen) at about 150° C. for about 5 hours. The copper-containing support material was then treated to deposit about 7 grams/liter each of palladium and gold, and about 0.53 gram/liter of magnesium by the modified roto-immersion method using the techniques of impregnation, fixing and reduction as described in Examples 7–12 and impregnated with potassium acetate as described in Comparative Example A. When tested for its function in the production of vinyl acetate as described in Comparative Example A, the product exhibited carbon dioxide and heavy ends selectivities of 8.38% and 1.07% respectively. The activity factor was 2.1.

We claim:

1. A process for the production of vinyl acetate by reaction of ethylene, oxygen and acetic acid as reactants comprising contacting said reactants with a catalyst comprising a porous support on the porous surfaces of which are deposited catalytically effective amounts of metallic palladium and gold, copper as the free metal or cupric acetate, and a fourth metal selected from the group consisting of magnesium, calcium, barium, and zirconium, as its oxide or mixture of oxide and free metal.

2. The process of claim 1 wherein said fourth metal is magnesium.

3. The process of claim 1 wherein said fourth metal is calcium.

4. The process of claim 1 wherein said fourth metal is barium.

5. The process of claim 1 wherein said fourth metal is zirconium.

6. The process of claim 1 wherein said catalyst contains an alkali metal acetate deposited on the catalyst.

7. The process of claim 6 wherein said alkali metal acetate is potassium acetate.

8. The process of claim 7 wherein potassium acetate is fed to the reaction together with said reactants.

* * * * *